US00PP20010P2

(12) United States Plant Patent
Theobald

(10) Patent No.: US PP20,010 P2
(45) Date of Patent: May 19, 2009

(54) ***LOMANDRA* PLANT NAMED 'SEASCAPE'**

(50) Latin Name: *Lomandra confertifolia ssp rubiginosa*
Varietal Denomination: Seascape

(75) Inventor: Dave Theobald, Merimbula (AU)

(73) Assignee: Southern Aurora Flora Pty. Ltd., Merimbula (AU)

( * ) Notice: Subject to any disclaimer, the term of this patent is extended or adjusted under 35 U.S.C. 154(b) by 0 days.

(21) Appl. No.: 11/890,191

(22) Filed: Aug. 4, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell

(57) ABSTRACT

A new and distinct cultivar of *Lomandra* plant named 'Seascape' characterized by a compact growth habit and narrow grey-green leaves.

1 Drawing Sheet

Botanical Classification: *Lomandra confertifolia* ssp *rubiginosa.*
Variety Denomination: 'Seascape'.

BACKGROUND OF THE INVENTION

The present Invention relates to a new and distinct cultivar of *Lomandra* plant, botanically known as *Lomandra confertifolia* ssp *rubiginosa,* and hereinafter referred to by the name 'Seascape'. The new cultivar was discovered and selected as a single plant growing within a bed of *Lomandra* plants in a greenhouse. The exact parents are unknown. The cultivar 'Seascape' was discovered in 2001 in Merimbula in the state of New South Wales, Australia.

The first asexual reproduction of the new *Lomandra* was in 2001 by division in Merimbula, New South Wales, Australia. The unique features of this new *Lomandra* are stable and reproduced true to type in successive generations of asexual reproduction.

SUMMARY OF THE INVENTION

The following traits have been repeatedly observed and are determined to be the unique characteristics of 'Seascape'. These characteristics in combination distinguish 'Seascape' as a new and distinct cultivar:

1. Compact growth habit.
2. Grey-green leaf color.
3. Narrow leaves.

The closest comparison cultivar is *Lomandra* 'SIR5'. *Lomandra* 'Seascape' is different from 'SIR5' in the following characteristics:

1. 'Seascape' has a more compact habit than 'SIR5'.
2. 'Seascape' has shorter leaves than 'SIR5'.
3. 'Seascape' has grey-green leaves. The leaves of 'SIR5' are green.
4. 'Seascape' has grey-purple basal shoots. The shoots of 'SIR5' are brown.

BRIEF DESCRIPTION OF THE PHOTOGRAPH

The accompanying photograph illustrates the distinguishing traits of *Lomandra* 'Seascape'.

The photograph at the top of the sheet is an overall view of a 16 month old plant.

The photograph at the bottom of the sheet is a close-up view of flowers.

The photographs were taken using conventional techniques and although colors may appear different from actual colors due to light reflectance it is as accurate as possible by conventional photographic techniques.

DETAILED BOTANICAL DESCRIPTION

The new *Lomandra* has not been observed under all possible environmental conditions. The phenotype may vary somewhat with variations in environment such as temperature and light intensity, without, however, any variance in genotype.

The following is a detailed description of the new *Lomandra* cultivar named 'Seascape'. Data was collected Merimbula, New South Wales, Australia from 16 month old plants raised in 20 cm. pots in commercial grade, soil-less potting mix. In the following description, color references are made to The Royal Horticultural Society Colour Chart, 1995 Edition.

Botanical classification: *Lomandra confertifolia* ssp *rubiginosa* cultivar 'Seascape'.
Parentage:
*Female parent.*—Unknown.
*Male parent.*—Unknown.
*Propagation.*—Tissue Culture or Division.
*Root description.*—Fine and fibrous.
Plant description:
*Growth habit.*—'Seascape' is a short, rhizomatous plant forming a compact tussock. Average plant height is 50 cm and average plant spread is 75 cm.
*Leaves.*—Shape, subulate; Width narrow 3–4 mm at base narrowing to the tip, average length 45 cm, upper and lower side color of leaf yellow-green (RHS 137A), surface texture strongly glaucous resulting in an overall foliage color gray-green approx (RHS 189A); leaf margin recurved, entire; leaf apex acute; venation pattern parallel, color yellow-green (RHS 137A); in cross-section, emerging new leaves flat and mature leaves concave.

*Basal sheath.*—Color grey-purple (187A).

*Rhizomes.*—Absent to very short.

*Inflorescence.*—Panicle, length 20-40 mm, average width 20–25 mm, male flowers only, predominant color of inflorescence at anthesis yellow (5A).

*Floret.*—Sessile, average length 3 mm, diameter 2.5 mm.

*Pedicels.*—Present. Length 4–5 mm, diameter 1–1.5 mm.

*Pedicel color.*—127A.

*Bracts.*—Number 4, length 2–3 mm, width 1–1.5 mm, apex acute, margin entire.

*Bract color.*—Grey-brown 200B.

Flowers:

*Tepals.*—3 free, shape elliptical, length 1–2 mm, width 1 mm, apex acute, base obtuse, margin entire.

*Tepal color.*—Upper surface red-purple 59A, lower surface red-purple 59A.

*Petals.*—Number 4, shape elliptical, length 3 mm, width 1.25 mm, apex acute, base obtuse, margin entire.

*Petal color.*—Upper surface yellow 5A, lower surface yellow 5A.

*Flower peduncle.*—Length 18 cm, diameter 3 mm, color 127A.

*Flowering period.*—From the spring through to mid-late fall in Australia.

*Lastingness of inflorescence.*—Approximately 3–4 weeks.

Reproductive organs: Female only.

Fragrance: Medium, typical of *Lomandra*.

Seed: Seed production has not been observed.

Environmental tolerances: Has shown potential for shade tolerance. The winter hardiness of is to −2° C. Excellent drought tolerance.

Disease Resistance: Good resistance to root rot.

Pest Resistance: Has not been observed.

What is claimed is:

1. A new and distinct variety of *Lomandra* plant named 'Seascape', as described and illustrated.

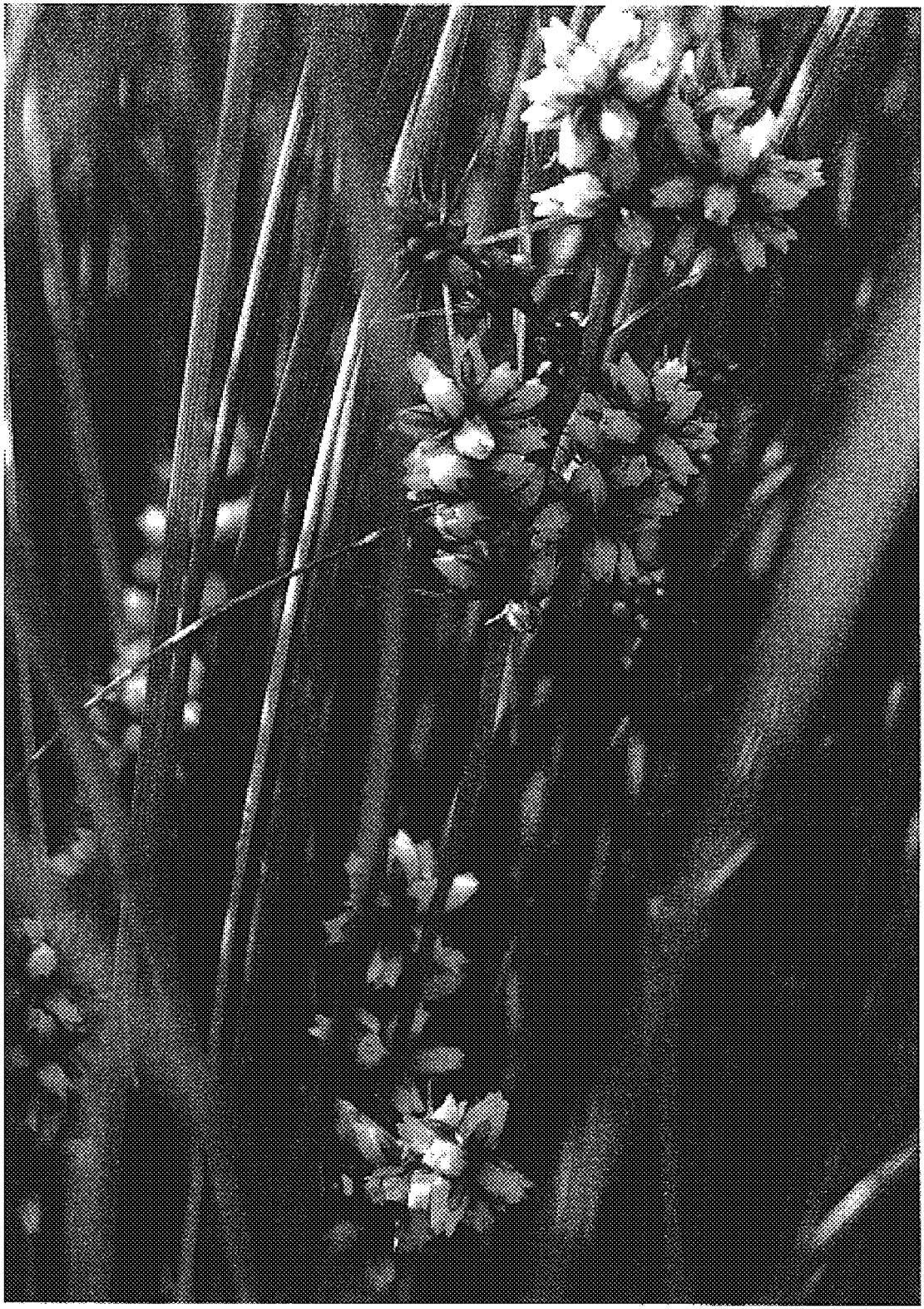

* * * * *